United States Patent [19]

Uriza

[11] 4,297,996
[45] Nov. 3, 1981

[54] STERILE BANDAGE AND TOURNIQUET

[76] Inventor: Eduardo C. Uriza, 949 - 3 Del Ejercito, Lima 18, Peru

[21] Appl. No.: 147,375

[22] Filed: May 7, 1980

[51] Int. Cl.³ .............................................. A61F 13/00
[52] U.S. Cl. ...................................... 128/169; 128/327
[58] Field of Search ............... 128/327, 169, 160, 165, 128/155, 156

[56] References Cited

U.S. PATENT DOCUMENTS

| | | | |
|---|---|---|---|
| 1,473,041 | 11/1923 | Henderson | 128/327 |
| 1,885,007 | 10/1932 | Rosenblatt | 128/327 X |
| 2,618,269 | 11/1952 | Baum et al. | 128/327 |
| 3,125,093 | 3/1964 | Hutchins | 128/169 X |
| 3,625,209 | 12/1971 | Clark | 128/169 |
| 3,954,109 | 5/1976 | Patel | 128/327 |

Primary Examiner—John D. Yasko
Attorney, Agent, or Firm—Harvey B. Jacobson

[57] ABSTRACT

An elastic bandage assembly is provided including an elongated absorptive pad having a transverse fold zone centrally intermediate its opposite ends dividing the pad into a pair of opposite end pad sections. The pad is folded along the fold zone with the end pad sections relatively angularly displaced between 40° and 90° and an elongated non-stretchable, flexible panel has its opposite ends anchored relative to the remote ends of the end pad sections with the panel being substantially straight and disposed on the included angle side of the pad when the pad sections are in the relatively angularly displaced positions thereof. An elongated flexible and stretchable bandage wrapping strip has one end thereof overlying and anchored relative to the excluded angle side of the pad and the wrapping strip is of a length at least several times the length of the pad and has a longitudinally extending slit formed in its other end opening endwise outwardly thereof to define a pair of tie straps.

9 Claims, 9 Drawing Figures

STERILE BANDAGE AND TOURNIQUET

BACKGROUND OF THE INVENTION

In many instances, a wound is incurred on a body limb and requires a pressure bandage. Further, in some instances a body limb wound requires the utilization of a tourniquet to prevent excess flow of blood from the wound. Accordingly, a need exists for an assemblage which may be utilized to form an effective pressure bandage or, alternately, to define a tourniquet, if needed.

Examples of various forms of pressure bandages and tourniquet constructions, including some of the general structural and operational features of the instant invention, are disclosed in U.S. Pat. Nos. 3,867,939, 3,885,560, 3,888,248 and 4,053,053. However, these previously known pressure bandage contructions are for the most part not constructed and packaged in a form enabling them to be applied in a manner substantially insuring sterile application to a wound. Further, some previously known bandage structures of this type also require a separate bandage wrapping strip in order to effect application of the pressure bandage to an associated wound in a pressure bandage-type situation and the utilization of a separate wrapping strip is sometimes difficult to effect by a single person and especially if that single person is also injured.

BRIEF DESCRIPTION OF THE INVENTION

The combined pressure bandage and tourniquet construction includes features thereof enabling sterile packaging and removal from the packaging and application to an associated wound in a sterile manner, even by an unskilled person who may be injured.

The construction further includes a bar to fix the tourniquet having tie straps anchored relative to one end thereof and which may be utilized, with the wrapping strip of the bandage, to form a readily operable tourniquet, when desired.

The main object of this invention is to provide a first aid-type of pressure bandage and tourniquet construction which may be readily utilized, in the form required, by even inexperienced persons.

Another object of this invention is to provide a pressure bandage and tourniquet construction including features thereof enabling the pressure bandage portion to be readily applied to a wounded person even by a person who may also be injured.

Yet another important object of this invention is to provide a pressure bandage construction which may be self applied with little effort by a wounded person.

A final object of this invention to be specifically enumerated herein is to provide a combined pressure bandage and tourniquet construction in accordance with the preceding objects and which will conform to conventional forms of manufacture, be of simple construction and easy to use so as to provide a device that will be economically feasible and readily appliable by inexperienced persons.

These together with other objects and advantages which will become subsequently apparent reside in the details of construction and operation as more fully hereinafter described and claimed, reference being had to the accompanying drawings forming a part hereof, wherein like numerals refer to like parts throughout.

DETAILED DESCRIPTION OF THE INVENTION

Figure 1:
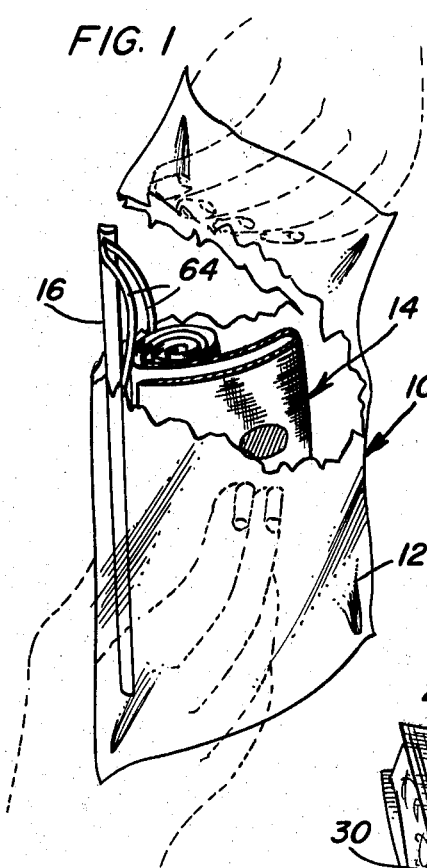
FIG. 1 is perspective view illustrating the manner in which the packaging for the combined pressure bandage and tourniquet may be readily opened.

Referring now more specifically to the drawings, the numeral 10 generally designates a packet including a tearable envelope 12 enclosing a pressure bandage assembly referred to in general by the reference numeral 14 and a holding or fixing bar 16. The envelope 12 is, of course, designed to maintain the assembly 14 and bar 16 in a sterile condition during storage and prior to use.

The assembly 14 comprises an elongated absorptive pad 18 including a transverse fold zone 20 centrallly inermediate its opposite ends dividing the pad 18 into a pair of opposite end pad sections 22 and 24.

The pad comprises first and second plies or elements 25 and 26 and each ply 25 and 26 comprises a pair of superposed gauze layers 28. A third element 30 of suitable absorptive material, such as cotton, is disposed between the plies 25 and 26 and corresponding marginal edges of the plies or elements 25 and 26 are sewn together by stitching 32 extending through the corresponding marginal portions of the third ply 30. In addition, the plies 25 and 26 are also sewn together along the fold zone 20, through the element 30, by stitching 33.

The pad 18 is folded along the fold zone 20 to a position with the pad end sections 22 and 24 relatively angularly disposed between 40° and 90° and a porous single or double gauze flexible panel 34 has its opposite ends anchored by stitching to the remote ends of the panel sections 22 and 24. The flexible panel 34 is provided to prevent the relatively folded portions of the pad 18 from being angularly extended to 180° positions and to thus enable a person to grip the pad 18 from the excluded angle side thereof to prevent contamination of the included angle side to be placed over a wound. The panel 34 is non-stretchable and is in a straight condition extending between the remote ends of the gauze sections 22 and 24 when the latter are disposed in 40° to 90° relatively angularly displaced positions, the flexible panel 34 extending across the included angle defined by the relatively angulated pad sections 22 and 24.

The excluded angle side of the pad 18 defining the exterior angle has one end portion 36 of an elongated flexible and elastic band wrapping bandage 38 secured thereover by readily removable stitching 39 and the remote end of the strip 18 has a transversely centered elongated longitudinally extending slit 40 formed therein opening endwise outwardly of the corresponding strip end and defining a pair of tie straps 42 and 44.

Figure 2:
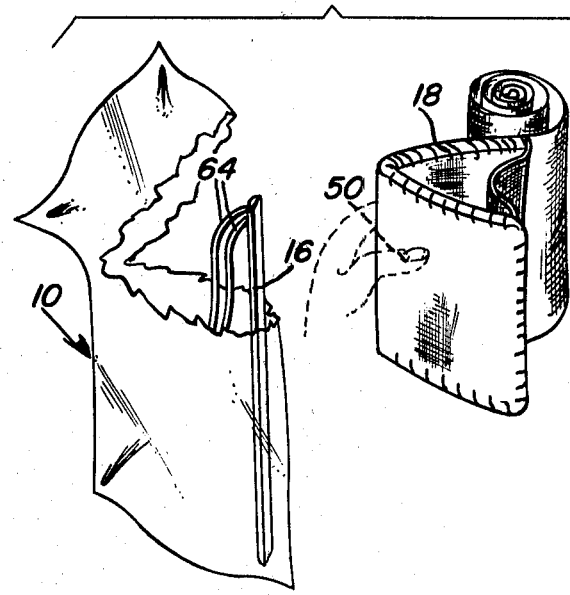
FIG. 2 is a perspective view illustrating the manner in which the pressure pad portion of the pressure bandage may be gripped without contaminating the side of the bandage to be applied over the wound during removal of the bandage from the packaging and its application to a wound.
Figure 9:
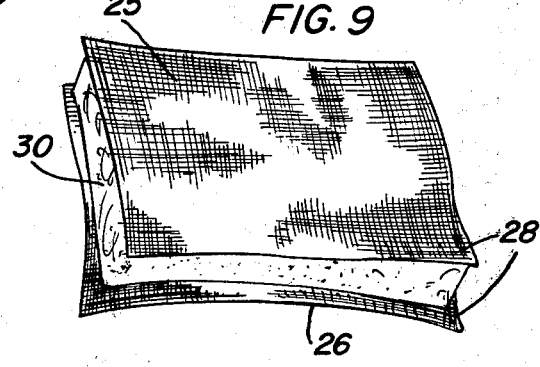
FIG. 9 is a perspective view of the pad illustrating the components of which the pad is in part constructed.
Figure 3:
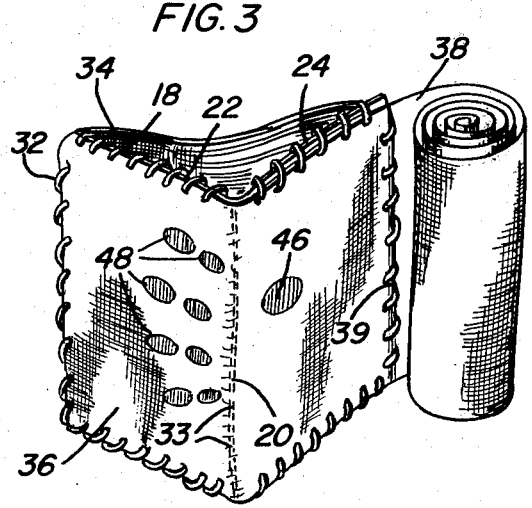
FIG. 3 is a further perspective view of the pressure bandage.

Also, it may be seen from FIG. 2 of the drawings that the outer side of the one end portion 36 of the band wrapping bandage 38 includes printed locations 46 and 48 on opposite sides of the fold zone 20. The location 46 designates the area of the outer side of the assembly 14 to be engaged by the thumb 50 of a person desiring to apply the assembly to a wound and the locations 48 indicate those areas of the outer side of the assembly 14 to be gripped by the four fingers opposing the thumb in order that the assembly 14 may be handled in a manner substantially assuring sterile application of the assembly 14 to a wound.

Figure 4:
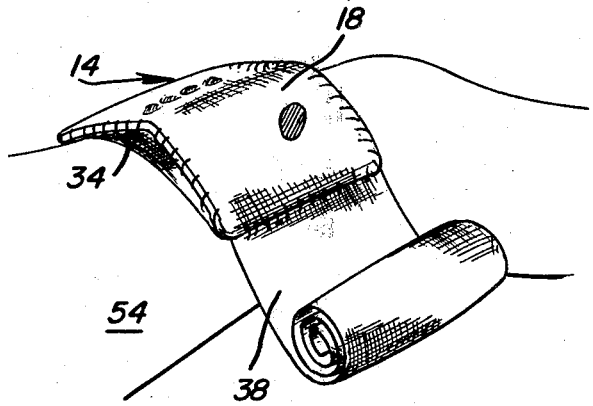
FIG. 4 is a perspective view illustrating the initial application of the pressure bandage to a wounded limb portion.

In applying the assembly 14 to a limb 54 in the manner illustrated in FIG. 4 of the drawings, it may be seen that the flexible panel 34 first contacts the wounded area and that inward pressure applied to the outer side of the pad 18 will cause the flexible panel 34 to engage the underlying wound portion in the manner of a pressure bandage. After the panel 18 has been applied to the wounded area in the manner illustrated in FIG. 4 of the drawings, the free end of the bandage wrapping strip 38 is wrapped about the associated limb area and tied in position thereon through the utilization of the tie straps 42 and 44 in the manner illustrated in FIG. 5 of the drawings. Accordingly, it may be seen that the panel 18 effectively forms a pressure bandage held in position through the utilization of the bandage wrapping strip 38.

Figure 7:
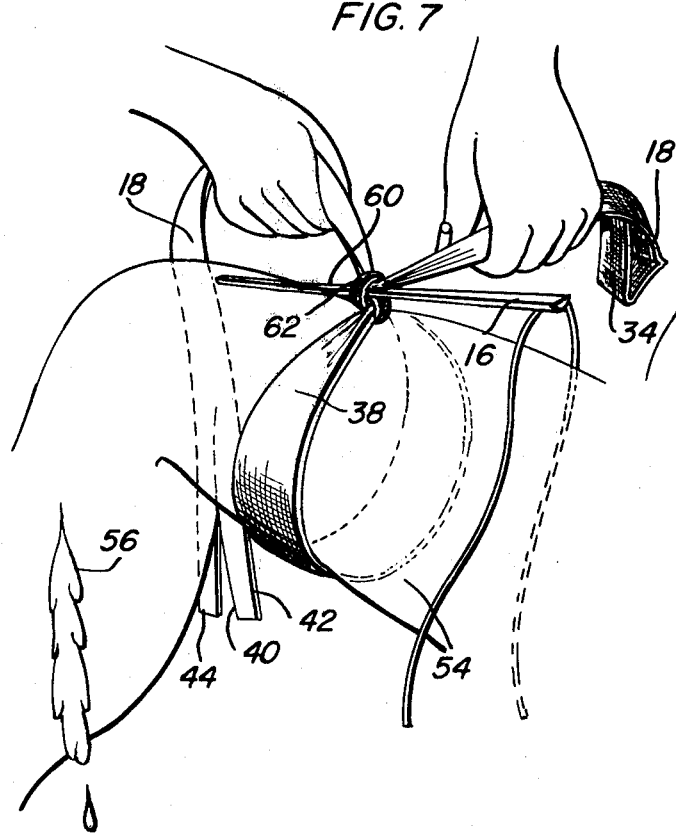
FIG. 7 is a perspective view illustrating initial utilization of the pressure bandage and tourniquet holding attachment in order to form a tourniquet.

If, however, the wound 56 involves a cut artery and the flow of blood from the wound may not be effectively stopped through utilization of the assembly 14 as a pressure bandage, the bandage wrapping strip 38 of the assembly 14 may be tied about the limb 54 in the manner illustrated in FIG. 7 of the drawings and with one end portion 60 of the bar 16 extending through the knot 62 formed in the bandage wrapping strip 38. After the bandage wrapping strip 38 has thus been applied about an upper portion of the limb 54, the rod 16 may be turned so as to tighten that portion of the bandage wrapping strip 38 extending about the limb 54 to form a tightened tourniquet and the tie tabs 64 carried by the opposite end of the rod 16 may be tied about the limb 54 in order to retain the tourniquet in a tightened condition about the limb 54.

Figure 5:
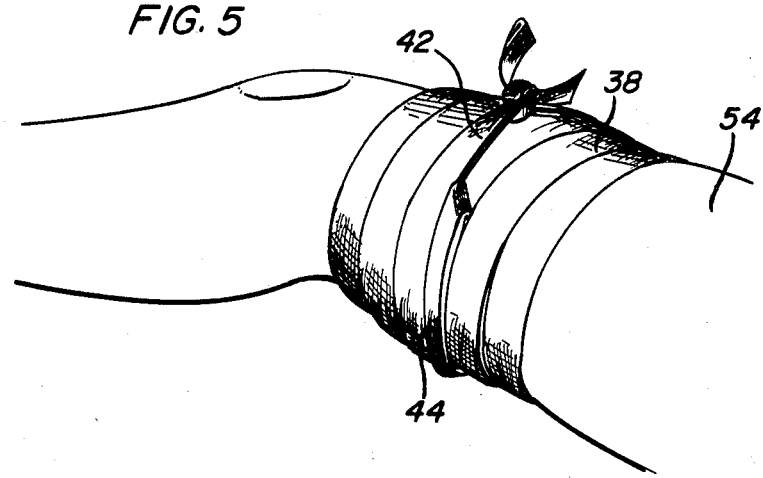
FIG. 5 is a perspective view of the wounded limb portion with the pressure bandage fully applied thereto.
Figure 6:
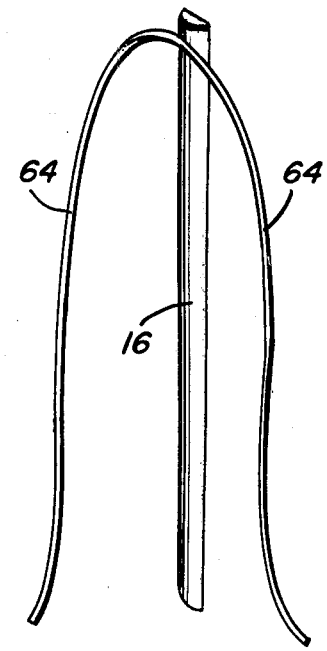
FIG. 6 is a perspective view of an accessory for fixing the bandage in place.
Figure 8:
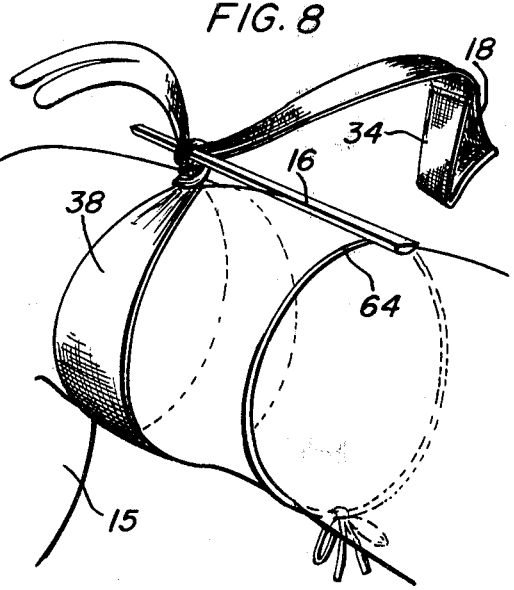
FIG. 8 is a perspective view similar to FIG. 7 illustrating the tourniquet completely formed.

It will thus be noted that the assembly 14 may be used either to form a pressure bandage in the manner illustrated in FIGS. 4 and 5 of the drawings or to form a tourniquet which may be readily loosened or tightened, as desired, in the manner illustrated in FIGS. 7 and 8 of the drawings. Further, the assembly 14 is constructed in a manner whereby its application to form a pressure bandage in the manner illustrated in FIG. 4 may be accomplished by even an inexperienced and injured person in a manner substantially assuring antiseptic application thereof. Of course, the envelope 12 maintains the entire assembly 14 sterile during storage thereof prior to its usage.

The foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as new is as follows:

1. A pressure bandage assembly, said assembly including an elongated absorptive pad including a transverse fold zone centrally intermediate its opposite ends dividing said pad into a pair of opposite end pad sections and along which said pad is folded to place said end pad sections in positions relatively angularly disposed between 40° and 90°, an elongated porous and flexible panel having its opposite ends anchored relative to the remote ends of said end pad sections, said panel being substantially and of a length to extend, in a longitudinally straight condition between said remote ends on the included angle side of said pad when said end pad sections are in said 40° to 90° relatively angulated positions.

2. The combination of claim 1 including an elongated flexible bandage wrapping strip of a width generally coinciding with the width of said pad and having one end overlying and anchored relative to the excluded angle side of said pad, said wrapping strip being of a length at least several times the length of said pad.

3. The combination of claim 2 wherein the other end of said wrapping strip has a central elongated longitudinally extending slit formed therein opening endwise outwardly of said wrapping strip other end and dividing the latter into a pair of tie strips.

4. The combination of claim 2 wherein said wrapping strip is constructed of elastic material and may be longitudinally stretched.

5. The combination of claim 2 wherein said one end of said wrapping strip substantially fully overlies the excluded angle side of said pad and includes longitudinally spaced transversely spaced zones thereof overlying and secured to the marginal portions of said remote ends.

6. The combination of claim 5 wherein said wrapping strip is constructed of elastic material and may be longitudinally stretched.

7. The combination of claim 6 wherein said wrapping strip one end is secured to said excluded angle side of said pad in a non-stretched condition.

8. The combination of claim 7 wherein the other end of said wrapping strip has a central elongated longitudinally extending slit formed therein opening endwise outwardly of said wrapping strip other end and dividing the latter into a pair of tie strips.

9. The combination of claim 2 including a tourniquet forming and holding assembly, said assembly including an elongated rigid bar having one end adapted to be received through a knot formed in opposite end portions of said wrapping strip after the latter is encircled loosely and tied about a limb, said bar being adapted to be swung about an axis transverse thereto and passing through said knot for tightening and loosening said wrapping strip about said limb, and a pair of elongated felxible tie tabs or strings supported from the other end of said bar for tieing about said limb to retain said bar in position substantially paralleling said limb.

* * * * *